(12) United States Patent
Davies et al.

(10) Patent No.: US 7,501,453 B2
(45) Date of Patent: Mar. 10, 2009

(54) CYCLOPROPANES WITH CENTRAL NERVOUS SYSTEM ACTIVITY

(75) Inventors: Huw M. L. Davies, E. Amherst, NY (US); Timothy Gregg, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 11/716,884

(22) Filed: Mar. 12, 2007

(65) Prior Publication Data

US 2007/0244201 A1    Oct. 18, 2007

Related U.S. Application Data

(60) Provisional application No. 60/781,245, filed on Mar. 10, 2006.

(51) Int. Cl.
*A61K 31/137* (2006.01)
*C07C 211/40* (2006.01)

(52) U.S. Cl. .................................. 514/650; 564/306
(58) Field of Classification Search .................. None
See application file for complete search history.

(56) References Cited

U.S. PATENT DOCUMENTS

| | | | |
|---|---|---|---|
| 5,227,385 A | 7/1993 | Caldwell et al. |
| 5,262,428 A | 11/1993 | Davies et al. |
| 5,288,872 A | 2/1994 | Davies et al. |
| 5,342,949 A | 8/1994 | Davies et al. |
| 5,591,854 A | 1/1997 | Davies |
| 5,760,055 A | 6/1998 | Davies |
| 5,763,455 A | 6/1998 | Davies et al. |
| 6,008,227 A | 12/1999 | Davies et al. |
| 6,013,242 A | 1/2000 | Davies et al. |

OTHER PUBLICATIONS

Agawa, et al., Reaction of Vinyl Supphone with α-Metallated Nitriles. J.C.S. Perkin I, Jun. 1980, pp. 751-755.

*Primary Examiner*—Samuel A Barts
(74) *Attorney, Agent, or Firm*—Hodgson Russ LLP

(57) ABSTRACT

Disclosed are aromatic cyclopropane compounds with CNS activity. These compounds can be used for alleviating symptoms of CNS disorders.

12 Claims, No Drawings

CYCLOPROPANES WITH CENTRAL NERVOUS SYSTEM ACTIVITY

This application claims priority to U.S. patent application Ser. No. 60/781,245, filed on Mar. 10, 2006, the entire disclosure of which is incorporated herein by reference.

This work was supported by Grant Nos. NO1 DA-18826 and 5R01DA15225-03 from the National Institutes of Health. The Government has certain rights in the invention.

FIELD OF THE INVENTION

The present invention relates generally disorders of the central nervous system and more particularly to alleviating symptoms of CNS disorders.

BACKGROUND OF THE INVENTION

Central Nervous System disorders are economically and socially devastating. For example, schizophrenia is one of the leading causes of disability worldwide with a lifetime prevalence of 0.6 to 1.3% characterized by high morbidity and mortality. Only less than 15% of people with this disability are competitively employed, whilst about 20% live independently.

Schizophrenia is generally characterized by positive symptoms (such as delusions, hallucinations, disorganized behavior), negative symptoms (such as anergia), affective symptoms (such as dysphoria, hopelessness, anxiety, hostility, aggression) and/or cognitive deficits.

Typical treatment for such disorders includes drugs that affect the monanine receptor systems. For example, the primary effect of first generation antipsychotics is dopamine (D2 receptor) blockade. While these are effective in treating the positive symptoms of schizophrenia, they exert modest effects on negative symptoms and cognitive deficits. Thus, despite the availability of some drugs for treating central nervous system disorders such as schizophrenia, there are many unmet needs for improved methods and compounds for treating central nervous system disorders.

SUMMARY OF THE INVENTION

The present invention provides aromatic cyclopropane compounds. The compounds of the present invention include compounds having the general formula:

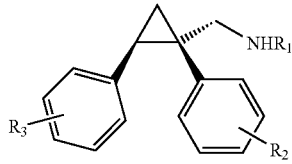

or its enantiomer [in which the cyclopropane carbon bearing the amino-containing substituents is in the R configuration (as opposed to S, as in the figure), and the remaining aryl-bonded propane carbon is in the S configuration (as opposed to R, as in the figure)], and racemic mixtures of the two enantiomers.

The group R1 can be selected from the group consisting of an alkane group having three or fewer carbons, and optionally, the amino nitrogen is present as a salt, such as, for example, a hydrochloric acid salt. The groups R2 and R3 can be one or more substituents selected from the group consisting of hydrogens, halogens, alkanes of 3 carbons or less, or adjacent rings, such that the R-bearing ring comprises a multi-tiring, conjugated group.

Also provided is a method for using the cyclopropane compounds to alleviate symptoms of CNS disorders. The method comprises administering to the individual a cyclopropane compound in an amount effective to reduce the symptoms of the CNS disorder. Such disease include but are not limited to broad spectrum psychosis such bipolar disorders, depression, mood disorders, addictions, cognitive disorders, and neurodegenerative diseases such as Alzheimer's disease, Parkinson's disease.

DESCRIPTION OF THE INVENTION

This invention provides novel compounds which can be used as therapeutic agents for CNS diseases and drug abuse. These compounds include aromatic cyclopropane compounds as described more fully below.

1,2-Diarylcyclopropylmethylamines

Monoamine transporter inhibitors have been shown to have great therapeutic utility. Selective serotonin transporter (SERT) inhibitors are some of the most widely used antidepressants. Non selective ligands binding to SERT as well as the norepinephrine transporter (NET) have also been launched as antidepressant agents. Dopamine transporter (DAT) inhibitors are used for the treatment of Attention Deficit Disorders, although DAT inhibitors such as cocaine can have abuse potential. Serotonin receptors are split into several sub-types and selective ligands for many of the sub types are useful therapeutic agents. 5-HT$_{2a}$ antagonists have been shown to have useful therapeutic potential as antidepressants and for other CNS disorders. Recently, promising results have been found for the use of 5-HT$_{2a}$ antagonists as therapeutic agents for cocaine addiction.

The compounds of the present invention include compounds having the general formula:

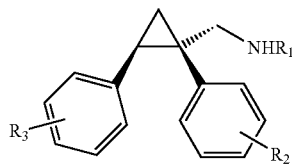

or its enantiomer [in which the cyclopropane carbon bearing the amino-containing substituents is in the R configuration (as opposed to S, as in the figure), and the remaining aryl-bonded propane carbon is in the S configuration (as opposed to R, as in the figure)], and racemic mixtures of the two enantiomers.

The group R1 can be selected from the group consisting of an alkane group having three or fewer carbons, and optionally, the amino nitrogen is present as a salt, such as, for example, a hydrochloric acid salt. The groups R2 and R3 can be one or more substituents selected from the group consisting of hydrogens, halogens, alkanes of 3 carbons or less, or adjacent rings, such that the R-bearing ring comprises a multi-tiring, conjugated group.

Preferably, R1 is a methyl group, and R2 and/or R3 consist of 1) hydrogen or 2) meta and para chlorine substitutions, or R3 consists of an adjacent ring at the 2 and 3 positions of the R3-bearing aryl ring such that the R3-bearing aryl ring comprises a naphthyl group.

Also included in the compounds of the present invention are compounds as described above, except the inclusion of heterocycle/compound/fused-ring structures in place of one or both of the aromatic rings indicated in the above structure. Examples of such structures may be pyridine, thiophene, pyrrole, furan, benzofuran, indole, benzothiophene, etc.

The aromatic/heterocyclic/fused ring structures may be substituted. Examples of include mono-, di- and tri-susbstituted substitutions with substituents such as consist of alkyl, alkenyl, alkoxy, halo, nitro, cyano, keto, amino, carboxylate, substituted or unsubstituted, or a combination thereof. The aromatic/heterocyclic/fused ring structures may be substituted. Examples of include mono-, di- and tri-susbstituted substitutions with substituents such as consist of alkyl, alkenyl, alkoxy, halo, nitro, cyano, keto, amino, carboxylate, substituted or unsubstituted aromatic, or a combination thereof.

The present invention also includes enantiomerically pure compositions comprising either the R,S or the S,R enantiomer mentioned above. As elucidated above, the preparation of a given enantiomer can be accomplished by using the proper enantiomer of the catalyst $Rh_2(DOSP)_4$ in the ring formation reaction . in Scheme 1, below. The invention also includes racemic mixtures of the R,S and S,R enantiomer. Such mixtures can be prepared by the use of mixtures of catalyst enantiomers, as well as by simply mixing the enantiomers in the desired ratio.

In particular embodiments, the present invention provides cis-1,2-diarylcyclopropanemthylamines which can be used as therapeutic agents for CNS disorders. Binding at the $5HT_{2a}$ receptor combined with selective binding at the monoamine transporter can be obtained with certain members of this class of compounds. The biological activity related to the functionality on the two aromatic rings and which enantiomer (mirror image) of the cyclopropanemethylamine is used.

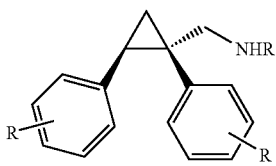

Chemistry

The basic scheme used in the synthesis of the cyclopropanes is shown for the 1-phenyl-2-naphthyl derivative 5 (Scheme 1). The first step is the rhodium catalyzed reaction of the phenyldiazoacetate 2 with the vinylnaphthalene 1. Either enantiomer of the cyclopropane 3 can be formed depending on which enantiomer of the catalyst $Rh_2(DOSP)_4$ is used. Conversion of 3 to the cyclopropanemethylamine 5 is achieved by reduction to the alcohol, oxidation to the aldehydes and then reductive amination. The scheme is very flexible because a range of aryldiazoacetates and vinyl substituted arenas could be used. Furthermore, a range of primary and secondary amines can be introduced in the reductive amination step.

Scheme 1

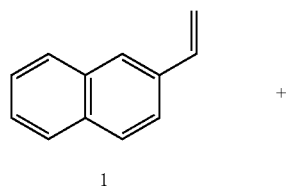

In another embodiment, the present invention provides a method for alleviating symptoms of CNS disorders. The method comprises administering to an individual a composition comprising an aromatic cyclopropane in an amount effective to reduce the symptoms of the CNS disorder.

The method of the invention is suitable for alleviating one or more symptoms of a variety of CNS disorders. Individuals with a CNS disorder frequently exhibit one or more symptoms that are characteristic of the particular disorder. It is also contemplated that a constellation of symptoms from multiple CNS disorders in the same individual can be alleviated by the present method. In this regard, recognizing symptoms from CNS disorders, and determining alleviation of said symptoms during or after practice of the present method is well within the purview of a person having ordinary skill in the art and can be performed using any suitable clinical, diagnostic, observational or other techniques. For example, symptoms of schizophrenia include but are not limited to delusions, hallucinations and catatonic behavior. A reduction in any of these particular symptoms resulting from practicing the method of the invention is considered an alleviation of the symptom. Particular CNS disorders presenting symptoms suitable for alleviation by the present method include but are not limited to: broad spectrum psychosis such as bipolar disorders, depression, mood disorders, drug addictions, cognitive disorders, and neurodegenerative diseases such as Alzheimer's disease and Parkinson's disease and combinations thereof.

Symptoms of each of these disorders are well known. Recognizing and determining a reduction in the symptoms of any of these particular disorders can be readily performed by those skilled in the art.

Compositions comprising an effective amount of the compound may be administered via any conventional route. Such routes include but are not limited to orally, parenterally, intramuscularly, intravenously and mucosally. In one embodiment, the route of administration is oral. Determining a dosage regimen of the compounds is well within the purview of those skilled in the art. By way of example, the dose levels may be from 4 micrograms per kilogram of body weight up to 50 milligrams/Kg of body weight. By way of another example, the dose may be from 20 micrograms/Kg up to 15 mg/Kg. It will be recognized by that dosing parameters, in addition to the weight of the individual, also take into account the age of the individual and the stage of the disease and can be determined according to conventional procedures.

Other components may be combined with the compounds to form pharmaceutical preparations for use in the present method. Such components can be selected depending on factors which include but are not limited to the dosage form, particular needs of the patient, and method of manufacture, among other things. Examples of such components include but are not limited to binders, lubricants, fillers, flavorings, preservatives, colorings, diluents, etc. Additional information regarding pharmaceutical composition components for use with the present method are described in Remington's Pharmaceutical Sciences (18$^{th}$ Edition, A. R. Gennaro et al. Eds., Mack Publishing Co., Easton, Pa., 1990). Accordingly, the selection of particular substances and their compatibilities with the compositions of the present invention can be readily ascertained by those of ordinary skill in the art. Additional details are provided in U.S. Pat. No. 5,763,455, which is incorporated herein by reference.

While the present invention is illustrated by way of the following examples, the examples are meant only to illustrate particular embodiments of the present invention and are not meant to be limiting in any way.

EXAMPLE 1

This Example provide representative techniques for making compounds of the invention.

(1S,2R)-methyl 2-(naphthalen-2-yl)-1-phenylcyclo-propanecarboxylate

Starting with 1.05 g (6.82 mmol) of 2-vinyl naphthalene, 1.01 g (5.71 mmol) of methyl 2-diazo-2-naphthylacetate and 0.075 g (0.040 mmol) of $Rh_2(S\text{-}DOSP)_4$, the ester 26 was obtained as a white solid. Yield: 1.28 g (4.23 mmol, 74%). The material was recrystallized from hexane to give material of >99% ee. $R_f$: 0.15 (9:1 hexane/ethyl ether); $^1$H NMR(300 MHz, $CDCl_3$) δ 7.78-7.91(m, 2H), 7.71 (d, J=8.5 Hz, 1H), 7.50-7.61(m, 3H), 7.24-7.37 (m, 5H), 7.04 (dd, J=8.5, 1.1 Hz, 1H), 3.85 (s, 3H), 3.56 (dd J=8.8, 7.7 Hz, 1H), 2.48 (dd J=4.9, 9.3 Hz, 1H), 2.46 (dd J=7.1, 5.2 Hz, 1H); $^{13}$C NMR (75 mHz, $CDCl_3$) δ 174.0 (C), 134.5 (C), 133.9 (C), 131.7 (CH), 127.5 (CH), 127.3 (CH), 126.9 (CH), 125.8 (CH), 125.6 CH), 125.1 (CH), 52.3 ($CH_3$), 37.4 (C), 33.1 (CH), 20.6 ($CH_2$); IR(neat) $cm^{-1}$ 3064, 3027, 1714, 1257, 729, 699; $[\alpha]_D^{25}$=−25.5° (c 0.65, $CHCl_3$); HPLC RR-Whelk, 5% i-PrOH/hexane, 1 ml/min $t_R$=9.3 min (minor), 10.7 min (major); mp 84-87° C.; Anal. calcd for $C_{21}H_{18}O_2$: C, 83.42; H, 6.00. Found C, 83.29; H, 5.94.

(1S,2R)-2-(naphthalen-2-yl)-1-phenylcyclopropan-ecarbaldehyde

A sample of 0.65 g (2.2 mmol) of ester 26 and 2.2 mmol $LiAlH_4$, gave the alcohol as a colorless oil. Yield 0.58 g (2.1 mmol 97%). $R_F$: 0.12 (4:1 hexane/ethyl acetate); $^1$H NMR (300 MHz, $CDCl_3$) δ 7.58-7.73 (m, 2H), 7.20-7.40 (m, 2H), 7.07-7.19 (m, 5H), 6.82 (dd, J=8.5, 1.7 Hz, 1H), 3.95 (d, J=11 Hz, 1H), 3.68 (d, J=11 Hz, 1H), 2.55 (dd, J=8.8, 6.0 Hz, 1H), 1.63 (dd, J=11, 5.8 Hz, 1H), 1.55 (m, 2H); IR(neat) $cm^{-1}$ 3350(br).

The crude alcohol was oxidized using Swern conditions to give the aldehyde as a white solid. Yield 0.49 g (1.8 mmol 95%); $R_f$ 0.38 (4:1 hexane/ethyl acetate); $^1$H NMR(300 MHz, $CDCl_3$) δ 9.7 (s, 1H), 7.60-7.70 (m, 2H), 7.57 (d, J=8.5 Hz, 1H), 7.40-7.43 (m, 3H), 7.13-7.19 (m, 4H), 6.9 (d, J=8.5 Hz, 2H), 3.2 (dd, J=8.5, 8.5 Hz, 1H), 2.20-2.30 (m, 2H). $^{13}$C NMR (75 MHz, $CDCl_3$), δ 200.6 (CH), 133.8 (C), 133.1 (C), 132.9 (C), 132.1 (C), 131.2 (CH), 128.3 (CH), 127.5 (CH), 127.4 (CH), 127.3 (CH), 127.0 (CH), 125.9 (CH), 125.8 (CH), 125.5 (CH), 46.5 (C), 35.8 (CH), 20.0 (CH2).

N-methyl((1R,2S)-2-(naphthalen-2-yl)-1-phenylcyclo-propyl)methanamine (5)Starting with 0.49 g (1.8 mmol) of aldehyde reductive amination with excess methylamine gave 0.23 g (0.88 mmol 44%) of 5 amine as a pale yellow oil. $R_f$ 0.30 (9:1 ethyl ether/triethylamine); $^1$H NMR (300 MHz, $CDCl_3$) δ 7.6-7.7 (m, 1H), 7.55-7.57 (m, 1H), 7.47 (d, J=8.5, 1H), 7.20-7.30 (m, 3H), 7.00-7.10 (m, 4H), 6.76 (dd, J=8.5, 1.3 Hz, 1H), 3.12 (d, J=12.0 Hz, 1H), 2.63 (d, J=12.1 Hz, 1H), 2.39-2.43 (m, 4H), 1.65 (dd, J=11.5 Hz, 1H), 1.47 (dd, J=8.8, 5.5 Hz, 1H); $^{13}$C NMR(75 MHz, CDCl3) δ 138.7 (C), 136.7 (C), 133.0 (C), 131.6 (C), 130.8 (CH), 128.0 (CH), 127.3 (CH), 127.2 (CH), 126.8 (CH), 126.4 (CH), 126.1 (CH), 126.0 (CH), 125.6 (CH),124.8 (CH), 63.0 ($CH_2$), 36.4 ($CH_3$), 36.0 (C), 28.5 (CH), 18.2 ($CH_2$).

A sample of 0.20 g (0.73 mmol) of the amine was converted to the hydrochloride salt with HCl in ether. The yellow solid was recrystallized from ethyl acetate/methanol to give the salt as white prisms. Yield 0.090 g (0.28 mmol, 39%). $^1$H NMR (300 MHz, $CD_3OD$) δ; 7.36-7.59 (m, 3H), 6.95-7.27 (m, 8H), 6.84 (d, J=8.2 Hz, 1H), 3.73 (d, J=12.9 Hz, 1H), 3.32-3.55 (m, 2H), 2.96 (d, J=12.9 Hz, 1H), 2.62 (dd, J=7.5, 7.5 Hz, 4H), 2.54 (s, 3H), 1.91 (dd, J=6.0, 6.0 Hz, 1H), 1.56 (dd, J=6.8, 6.8 Hz, 1H); Anal. calcd for $C_{21}H_{22}ClN$: C, 77.88; H 6.85; N, 4.32. Found: C, 77.74; H, 7.00, N 4.33.

EXAMPLE 2

This Example provides a demonstration of the effects of particular embodiments of the invention on neuroreceptors.

Monoamine Reuptake Binding Methods

Unknowns are weighed and dissolved in DMSO to make a 10 mM stock solution. An initial dilution to 50 μM in assay buffer for binding, or to 1 mM in water for uptake, is made. Subsequent dilutions are made with assay buffer supplemented with DMSO, maintaining a final concentration of 0.1% DMSO. Pipetting is conducted using a Biomek 2000 robotic workstation.

Inhibition of Radioligand Binding of [125I]RTI-55 to hDAT, hSERT or hNET in Colonla Cells Cell preparation: HEK293 cells expressing hDAT, hSERT or hNET inserts are grown to 80% confluence on 150 mm diameter tissue culture dishes and serve as the tissue source. Cell membranes are prepared as follows. Medium is poured off the plate, and the plate is washed with 10 ml of calcium- and magnesium-free phospate-buffered saline. Lysis buffer (10 ml; 2 mM HEPES with 1 mm EDTA) is added. After 10 min, cells are scraped from plates, poured into centrifuge tubes, and centrifuged 30,00×g for 20 min. The supernatant fluid is removed, and the pellet is resuspended in 12-32 ml of 0.32 m sucrose using a Ploytron at setting 7 for 10 sec. The resuspension volume depends on the density of binding sites within a cell line and is chosen to reflect binding of 10% or less to the total radioactivity.

Assay conditions: Each assay tube contains 50 µl of membrane preparation (about 10-15 µg of protein), 25 µl of unknown compound used to define non-specific binding, or buffer(Krebs-HEPES, pH 7.4;122 mM NaCl, 2.5 mM CaCl2, 1.2 mM MgSO4, 10 µM pargyline, 100 µM tropolone,0.2% glucose and 0.2% ascorbic acid, buffered with 25 mM HEPES) 25 Ml of [125I]RTI-55 (40-80 pM final concentration) and additional buffer sufficient to bring up the final volume to 250 µl. Membranes are preincubated with unknowns for 10 min prior to the addition of [125I]RTI-55. The assay tubes are incubated to 25° C. for 90 min. Binding is terminated by filtration over GF/F filters using Tomtec 96-well cell harvester. Fliter are washed for six seconds with ice cold saline. Scintillation fluid is added to each square and radioactivity remaining on the filter is determined using Wallac µ- or beta plate reader. Specific binding is defined as the difference in binding observed in the presence and absence of 5 µM mazindol (HEK-hDAT and HEK-hNET) or 5 M imipramine (HEK-hSERT). Two or three independent competition experiments are conducted with duplicate determinations. GraphPAD Prism is used to analyze the ensuing data, with IC50 values converted to Ki values using the Cheng-Prusoff equation (Ki=IC50/(1+([125I]RTI-55/KdRTI55))).

Receptor Binding Assay Methods

5HT1A Receptor

HA7 Cells (human receptor) are grown to confluence in DMEM containing 10% fetal bovine serum (FBS), 0.05% penicillin-streptomycin (pen-strep), and 400 µg/mL of Geneticin (G418). The cells are scraped from 100×20 mm plates and centrifuged at 500 g for 5 minutes. The pellet is homogenized in 50 mM Tris-HCl (pH 7.7), with a polytron, centrifuged at 27,000×g and resuspened at 10 mg protein/mL in the same buffer. The homogenate is then stored at −70 ° C. in 1-mL aliquots.

The thawed cells are washed once and resuspended at 10 mg protein/80 mL in 25 mM Tris-HCI containing 100 µM ascorbic acid in 10 µM nialamide at pH 7.4. the assay is performed in triplicate in 96-well plate. 100 µl of test compound or buffer and 0.80 mL of cell homogenate (0.10 mg protein/well) are added to 10 µl of [3H]8-OH-DPAT (0.5 nM final concentration). Non specific binding is determined with 1.0 µM dihyderoergotamine. The plates are incubated at 25° C. for 60 minutes and then filtered through glass fiber filter paper on a Tomtec cell harvester. The filters were washed four times with cold 50 mM Tris-HCl(pH 7.7) dried over night, and bagged with 10 mL scintillation cocktail before counting for 2 minutes on a Wallac Betaplate 1205 liquid scintillation center.

5-HT2A Receptor

NIH-3T3-GF6 cells (rat receptor) are grown as described for the HA7 cells. The cells are thawed, resuspended in 50 mM Tris-0HCl, and centrifuged at 27,000×g for 12 minutes. The pellet is then resuspened in 1 mg protein/80 mL in 25 mM Tris-HCl(pH7.7) and 0.80mL of cell homogenate(0.01 mg protein/well) is added to wells containing 100 µl of the test drug or buffer and 100 µl of [3H]ketanserin(0.40 nM final concentration). The plates are incubated at 25° C. for 60 minutes. Nonspecific binding is determined with 1.0 µM ketanserin.

5-HT2C Receptor

NIH-3T3-Pø cells (rat receptor) are grown as described for the HA7 cells. The final pellet is resuspended at 3 mg protein/80 mL in 50 mM Tris-HCl(pH7.7) 4 mM CaCl2, 10 µM pargyline and 0.1% ascorbic acid. Wells containing 100 µl of test drug or buffer, 100 µl of [3H]mesurlergine (0.40 nM final conc) and 0.80 ML of cell homogenate (0.03 mg protein/well) are incubated at 25° C. for 60 minutes. Nonspecific binding is determined with 10 µM mesurlergine.

Biological Activity

The biological data of representative diarylcyclopropanemethylamines are assayed as described in this Example are shown in table 1. The table consists of pairs of enantiomers; selectity is distinct for each. This can be seen in entry 1 and 2. The (1S, 2R) enantiomer binds with reasonable potency to SERT, NET and 5-HT2a while the (1R,2S) enantiomer is selective for SET. The 1 -aryl group has profound effect on the monamine transporter affinity. Very high affinity is obtained when the 1-aryl group is 3,4-dichlorphenyl and 2-naphthyl. The biological data indicate that the 1,2-diarylcyclproanemethylamines are a class of agents that would be useful for the treatment of CNS disorders.

TABLE 1

| Structure | CTDP # | Transporter | | | Receptor Class | | | | | |
|---|---|---|---|---|---|---|---|---|---|---|
| | | SERT (nM) | DAT (nM) | NET (nM) | $5\text{-}HT_{1A}$ (nM) | $5\text{-}HT_{2A}$ (nM) | $5\text{-}HT_{2C}$ (nM) | $D_1$ (nM) | $D_2$ (nM) | $D_3$ (nM) |
|  | 32,219 | 114 | 218 | 1869 | >10,000 | 206 | 564 | >10,000 | 1419 | >10,000 |

TABLE 1-continued

| Structure | CTDP # | Transporter | | | Receptor Class | | | | | |
|---|---|---|---|---|---|---|---|---|---|---|
| | | SERT (nM) | DAT (nM) | NET (nM) | 5-HT$_{1A}$ (nM) | 5-HT$_{2A}$ (nM) | 5-HT$_{2C}$ (nM) | D$_1$ (nM) | D$_2$ (nM) | D$_3$ (nM) |
| (S)(R) 3,4-diCl-phenyl / phenyl / NHCH₃·HCl | 32,220 | 45 | 1450 | 1460 | >10,000 | 7330 | >10,000 | >10,000 | 1576 | >10,000 |
| (R)(S) phenyl / 3,4-diCl-phenyl / NHCH₃·HCl | 32,221 | 1040 | 1380 | 3134 | >10,000 | 109 | 904 | >10,000 | 2639 | 2171 |
| (S)(R) phenyl / 3,4-diCl-phenyl / NHCH₃·HCl | 32,222 | 4600 | 6600 | >10,000 | >10,000 | 2996 | >10,000 | >10,000 | >10,000 | >10,000 |
| (S)(R) 3,4-diCl-phenyl / 3,4-diCl-phenyl / NHCH₃ | 32694 | 1527 | 1260 | 3700 | 4409 | 783 | 5,628 | 6,735 | 2,498 | 2,490 |
| (R)(S) 3,4-diCl-phenyl / 3,4-diCl-phenyl / NHCH₃ | 32695 | 172 | 730 | 2900 | 3884 | 39 | 499 | 6791 | 1098 | 2166 |
| (S)(R) phenyl / phenyl / NHCH₃ | 32696 | >7300 | 4650 | 4300 | >10,000 | >10,000 | >10,000 | >10,000 | >10,000 | >10,000 |
| (R)(S) phenyl / phenyl / NHCH₃ | 32697 | >10,000 | >5300 | 3900 | >10,000 | 2,950 | 4,714 | >10,000 | >10,000 | >10,000 |

TABLE 1-continued

| Structure | CTDP # | Transporter | | | Receptor Class | | | | | |
|---|---|---|---|---|---|---|---|---|---|---|
| | | SERT (nM) | DAT (nM) | NET (nM) | $5\text{-}HT_{1A}$ (nM) | $5\text{-}HT_{2A}$ (nM) | $5\text{-}HT_{2C}$ (nM) | $D_1$ (nM) | $D_2$ (nM) | $D_3$ (nM) |
| 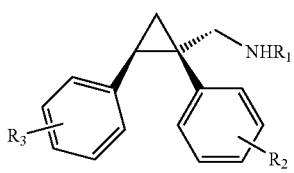 | 32698 | 14 | 1600 | 1270 | >10,000 | 5,304 | 8,863 | >10,000 | 1,384 | >10,000 |

The foregoing description of the specific embodiments is for the purpose of illustration and is not to be construed as restrictive. From the teachings of the present invention, those skilled in the art will recognize that various modifications and changes may be made without departing from the spirit of the invention.

We claim:

1. A compound having the following structure:

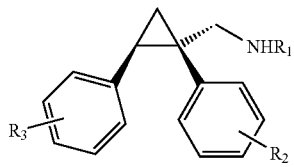

or its enantiomer, wherein R1 is an alkane of 3 carbons or less, R2 consists of one or more substituents selected from the group consisting of hydrogen, halogen, alkane of 3 carbons or less, and adjacent ring forming a naphthyl group, and R3 consists of one or more substituents selected from the group consisting of hydrogen, halogen, alkane of 3 carbons or less, and adjacent ring forming a naphthyl group.

2. A compound as in claim 1 wherein R1 is a methyl group, and wherein, optionally, the amino nitrogen is present as a hydrochloric acid salt.

3. A compound as in claim 2 wherein either R2 or R3 consist of hydrogen substituents.

4. A compound as in claim 2 wherein either R2 or R3 consist of p- and m-chlorine substituents.

5. A compound as in claim 2 wherein both R2 and R3 consist of p- and m-chlorine substituents.

6. A compound as in claim 1 wherein R3 is an adjacent ring forming a 2-naphthyl group.

7. A racemic mixture of the S,R and R,S enantiomers of a compound having the following structure:

wherein R1 is an alkane of 3 carbons or less, R2 and R3 independently consist of one or more substituents selected from the group consisting of hydrogen, halogen, alkane of 3 carbons or less, alkenyl, alkoxy, halo, nitro, cyano, keto, amino, carboxylate, adjacent ring forming a naphthyl group, and a combination thereof.

8. A racemic mixture as in claim 7 wherein R1 is a methyl group, and wherein, optionally, the amino nitrogen is present as a hydrochloric acid salt.

9. A racemic mixture as in claim 8 wherein either R2 or R3 consist of p- and m-chlorine substituents.

10. A racemic mixture as in claim 8 wherein both R2 and R3 consist of p- and m-chlorine substituents.

11. A racemic mixture as in claim 7 wherein R3 is an adjacent ring forming a 2-naphthyl group.

12. A method for alleviating one or more symptoms of a CNS disorder in an individual comprising administering to the individual a composition comprising a compound as in claim 1 in an amount effective to alleviate the symptoms of the CNS disorder, and wherein the administration of the composition alleviates one or more symptoms of the CNS disorder.

* * * * *